(12) United States Patent
Mehta et al.

(10) Patent No.: US 12,171,967 B2
(45) Date of Patent: Dec. 24, 2024

(54) PROXIMAL VENTRICULOPERITONEAL SHUNT WITH RETRACTABLE MESH

(71) Applicant: THE BOARD OF TRUSTEES OF THE UNIVERSITY OF ILLINOIS, Urbana, IL (US)

(72) Inventors: Ankit Mehta, Chicago, IL (US); James Ryoo, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 166 days.

(21) Appl. No.: 17/898,385

(22) Filed: Aug. 29, 2022

(65) Prior Publication Data

US 2023/0310815 A1    Oct. 5, 2023

Related U.S. Application Data

(60) Provisional application No. 63/327,407, filed on Apr. 5, 2022.

(51) Int. Cl.
*A61M 27/00* (2006.01)
*A61F 2/966* (2013.01)

(52) U.S. Cl.
CPC .......... *A61M 27/006* (2013.01); *A61F 2/966* (2013.01); *A61M 2205/3331* (2013.01)

(58) Field of Classification Search
CPC ........ A61M 27/006; A61M 2205/3331; A61M 27/00; A61F 2/966
See application file for complete search history.

(56) References Cited

U.S. PATENT DOCUMENTS

| | | | | |
|---|---|---|---|---|
| 4,610,658 A | * | 9/1986 | Buchwald | A61M 27/006 604/9 |
| 4,767,400 A | * | 8/1988 | Miller | B29C 53/587 604/8 |
| 4,950,232 A | * | 8/1990 | Ruzicka | A61M 27/006 604/43 |
| 5,385,541 A | * | 1/1995 | Kirsch | A61B 18/24 604/9 |
| 5,725,571 A | * | 3/1998 | Imbert | A61F 2/95 623/1.11 |
| 6,579,302 B2 | * | 6/2003 | Duerig | A61B 17/22 606/198 |
| 8,317,748 B2 | * | 11/2012 | Fiorella | A61M 25/1027 604/103.08 |

(Continued)

*Primary Examiner* — Benjamin J Klein
(74) *Attorney, Agent, or Firm* — GrowIP Law Group LLC

(57) ABSTRACT

The disclosure provides example shunt apparatus and methods for deploying the apparatus. The apparatus includes (a) an inner catheter having first and second ends, where the inner catheter has a plurality of fenestrations extending along a portion of the inner catheter, (b) an outer catheter, where the inner catheter is positioned at least partially within a lumen of the outer catheter, (c) a deployment wire moveably arranged in a lumen of a conduit that is coupled to the outer catheter, and (d) a mesh arranged surrounding at least the first end of the inner catheter, where the mesh has a first end coupled to the inner catheter and the mesh has a second end coupled to the deployment wire, where the mesh is configured to move between a first position in an unexpanded condition having the form of a sheath to a second position in an expanded condition.

20 Claims, 4 Drawing Sheets

(56) References Cited

U.S. PATENT DOCUMENTS

| | | | | |
|---|---|---|---|---|
| 2003/0078537 A1* | 4/2003 | Jang | A61M 25/104 | 604/528 |
| 2003/0135147 A1* | 7/2003 | Rosenberg | A61M 27/006 | 604/8 |
| 2005/0096691 A1* | 5/2005 | Groothuis | A61B 17/12136 | 606/200 |
| 2007/0129746 A1* | 6/2007 | Mische | A61N 1/36082 | 606/191 |
| 2008/0249458 A1* | 10/2008 | Yamasaki | A61M 27/006 | 604/8 |
| 2009/0137942 A1* | 5/2009 | Ei Shafei | A61M 27/006 | 604/8 |
| 2010/0222732 A1* | 9/2010 | Sevrain | A61M 27/006 | 604/8 |
| 2012/0101413 A1* | 4/2012 | Beetel | A61B 18/1492 | 601/3 |
| 2014/0243703 A1* | 8/2014 | Schmidt | A61B 5/031 | 600/561 |
| 2015/0297874 A1* | 10/2015 | East | A61M 39/225 | 604/9 |
| 2016/0136398 A1* | 5/2016 | Heilman | A61M 25/0108 | 604/9 |
| 2018/0104459 A1* | 4/2018 | Anand | A61M 39/223 | |
| 2019/0117945 A1* | 4/2019 | B?rgesen | A61M 27/006 | |
| 2021/0322653 A1* | 10/2021 | Thiagarajan | A61F 11/202 | |
| 2021/0353921 A1* | 11/2021 | Subramaniam | A61N 27/006 | |
| 2022/0203077 A1* | 6/2022 | Folan | A61F 2/04 | |
| 2022/0401111 A1* | 12/2022 | Rogers | A61B 17/0057 | |
| 2023/0173239 A1* | 6/2023 | Bae | A61M 27/002 | 604/9 |

* cited by examiner

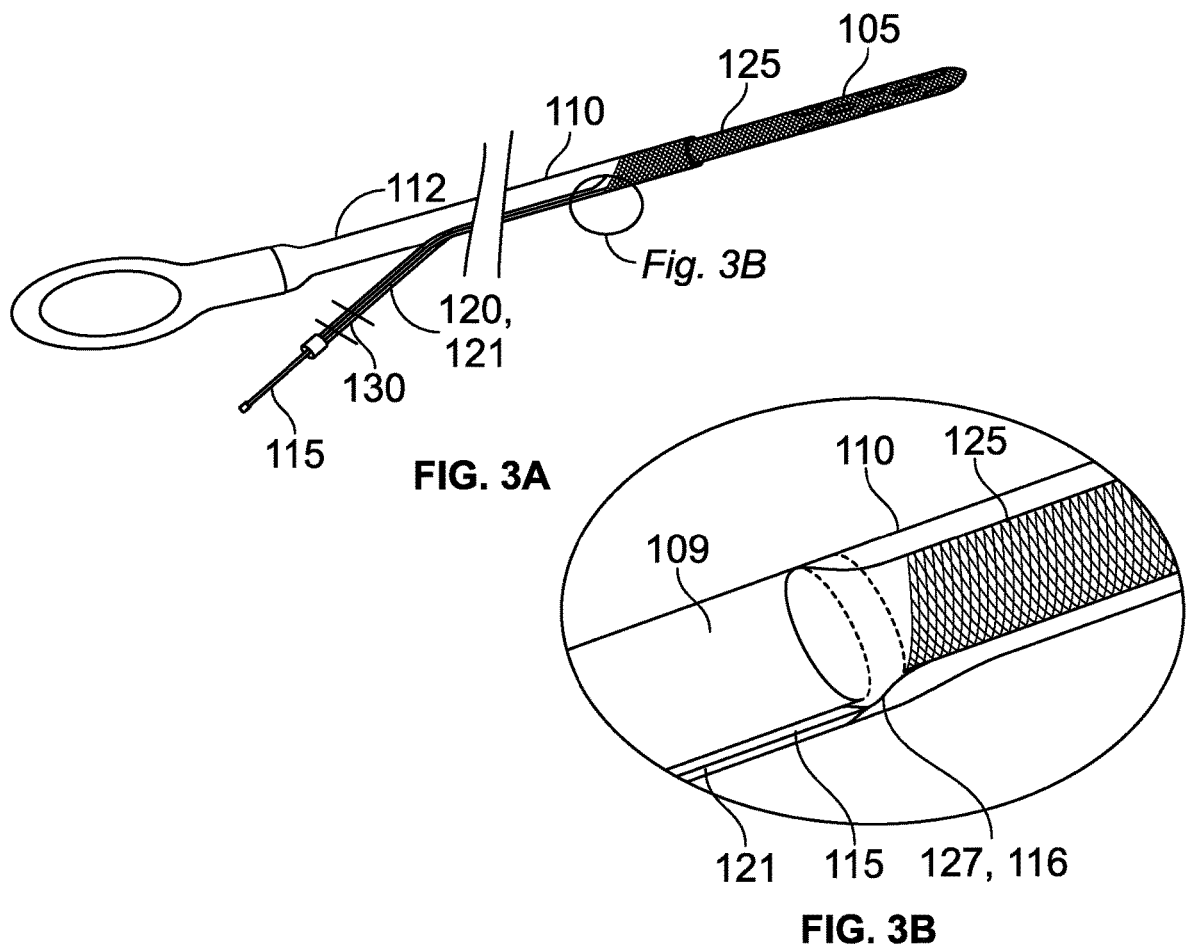
FIG. 3A
FIG. 3B
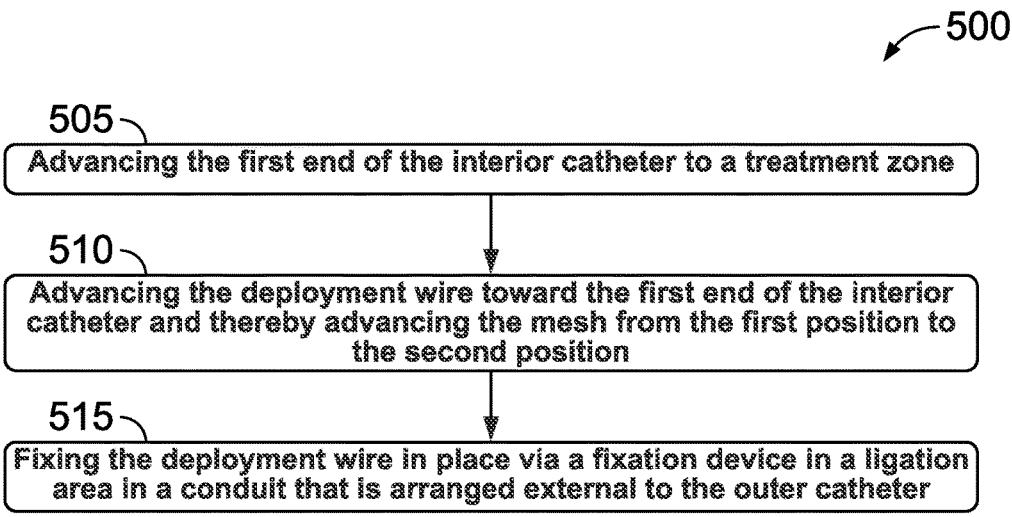
FIG. 5

PROXIMAL VENTRICULOPERITONEAL SHUNT WITH RETRACTABLE MESH

CROSS-REFERENCE TO RELATED APPLICATION

This U.S. Non-Provisional Patent Application claims priority to U.S. Provisional Patent Application No. 63/327,407, filed on Apr. 5, 2022, which is hereby incorporated by reference in its entirety.

BACKGROUND

The onset of hydrocephalus, a pathological buildup of fluid within the cerebral ventricles, often warrants neurosurgical intervention to divert excess fluid by means of inserting a Ventriculoperitoneal shunt ("VP shunt"). Hydrocephalus is caused by an imbalance between how much cerebrospinal fluid is produced and how much is absorbed into the bloodstream.

The VP shunt provides a conduit for fluid flow from the ventricles to the abdomen, thereby relieving the buildup of fluid caused by the imbalance. It consists of a proximal catheter inserted into the ventricle, a programmable shunt valve to control flow-rate, and a distal catheter, which empties into the abdominal cavity.

Shunt failure is a common complication for VP shunts requiring urgent removal and replacement of the malfunctioning unit. Shunt malfunction is most commonly caused by obstruction of the proximal catheter by the choroid plexus, ventricular ependyma, or "brain debris". Such obstructions remain an elusive problem, despite developments in shunt design and an increased emphasis in proper placement. Hospital admissions related to shunt revisions and replacements continue to accrue billions of dollars in medical costs per year, imposing a significant financial burden on the healthcare system.

The complication rates following insertion of a shunt tend to be high. Complications related to shunt insertion can include, for example shunt blockage, over drainage, under drainage, shunt infection, peritonitis, pseudocyst etc.

Shunt failure and malfunction are common complications that require urgent removal and replacement of the malfunctioning unit. In fact, as many as half of all shunt installations require replacement or revision.

SUMMARY

The disclosure provides a shunt apparatus and methods for deploying the shunt apparatus in a treatment zone. Exemplary shunt apparatus and methods disclosed herein offer a preventative solution to proximal catheter obstruction caused by attachment to the choroid plexus (or other adjacent brain structures) or aspiration of free-floating brain debris. The catheter includes a mesh that advantageously provides a protective structure that maintains the fenestrations of the shunt remain patent even after suboptimal placement (i.e. placement near the choroid plexus or ventricular wall) and simultaneously functions as a filter to prevent aspiration of debris which would otherwise clog the shunt. Accordingly, the shunt apparatus and methods may beneficially reduce the rates of VP shunt revisions due to proximal catheter obstruction.

Further, exemplary devices herein offer a relatively simple, mechanical solution to a complicated issue without introducing significant causes of harm. The mesh can include one or more portions composed of a pliable, MM-compatible, and biocompatible material that will neither introduce mechanical injury to the brain parenchyma nor cause an immune reaction. In addition, the expandability and retractability of the mesh allows for routine placement or removal of the shunt without a need to modify the current standard neurosurgical technique for shunt removal.

In a first aspect, an example shunt apparatus is disclosed. The shunt apparatus includes (a) an inner catheter having a first end and a second end, where the inner catheter has a plurality of fenestrations extending along a portion of the first end of the inner catheter and in fluid communication with a lumen of the inner catheter, (b) an outer catheter, where the inner catheter is positioned at least partially within a lumen of the outer catheter, (c) a deployment wire moveably arranged in a lumen of a conduit that is coupled to the outer catheter, where the lumen of the conduit is in communication with the lumen of the outer catheter such that a portion of the deployment wire is moveable within the outer catheter, and (d) a mesh arranged surrounding at least the first end of the inner catheter, where the mesh has a first end coupled to a proximal tip of the first end of the inner catheter and the mesh has a second end housed in the outer catheter and coupled to a first end of the deployment wire, where, in response to movement of the deployment wire, the mesh is configured to move between a first position in an unexpanded condition having the form of a sheath to a second position in an expanded condition.

In a second aspect, an example method for deploying the shunt apparatus according to the first aspect. The method includes (a) advancing the first end of the inner catheter to a treatment zone, (b) advancing the deployment wire toward the first end of the inner catheter and thereby advancing the mesh from the first position to the second position, and (c) fixing the deployment wire in place via a fixation device in a ligation area in a conduit that is arranged external to the outer catheter.

The features, functions, and advantages that have been discussed can be achieved independently in various examples or may be combined in yet other examples further details of which can be seen with reference to the following description and drawings.

BRIEF DESCRIPTION OF THE DRAWINGS

FIG. 3A illustrates a side view of the shunt apparatus having a conduit arranged external to the outer catheter with a deployment wire disposed therein and coupled to the mesh, according to one example implementation;

FIG. 3A;

FIG. 3B shows a detail view of the deployment wire coupled to the mesh from FIG. 4A shows a side view of the shunt apparatus with the mesh in a first position in an unexpanded condition having the form of a sheath, according to one example implementation;

FIG. 5 shows a flow diagram of a method for deploying the shunt apparatus, according to one example implementation.

Figure 1A:
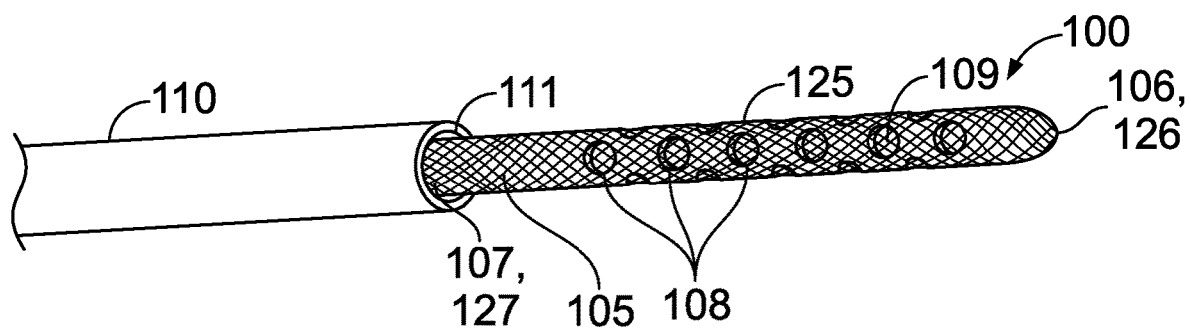
FIG. 1A is a side view of the shunt apparatus with the mesh in a first position in an unexpanded condition having the form of a sheath, according to one example implementation.

The drawings are for the purpose of illustrating examples, but it is understood that the inventions are not limited to the arrangements and instrumentalities shown in the drawings.

DETAILED DESCRIPTION

As used herein, "proximal" with respect to a portion or features of the apparatus refers to the end of the device (when in use) nearer the treatment zone (e.g., a ventricle of the brain) of the subject and the term "distal" means the portion or features of the device (when in use) further away from the treatment zone of the subject and nearer the access site and the operator.

As used herein, "first end" refers to a proximal end of the shunt apparatus or component thereof, and "second end" refers to a distal end of the shunt apparatus or component thereof.

FIGS. 1A-4E depict a shunt apparatus 100 that includes an inner catheter 105 having a first end 106 and a second end 107. The inner catheter 105 has a plurality of fenestrations 108 extending along a portion of the first end 106 of the inner catheter 105 and in fluid communication with a lumen 109 of the inner catheter 105. The shunt apparatus 100 further includes an outer catheter 110. The inner catheter 105 is positioned at least partially within a lumen 111 of the outer catheter 110.

The shunt apparatus 100 also includes a deployment wire 115 moveably arranged in a lumen 121 of a conduit 120 that is coupled to the outer catheter 110. The lumen 121 of the conduit 120 is in communication with the lumen 109 of the outer catheter 110 such that a portion of the deployment wire 115 is moveable within the outer catheter 110. The deployment wire 115 can either integrally formed with a mesh 125 (discussed below) or fixedly attached thereto, as illustrated in FIG. 3.

And the shunt apparatus 100 includes a mesh 125 arranged surrounding at least the first end 106 of the inner catheter 105. The mesh 125 has a first end 126 coupled to a proximal tip of the first end 106 of the inner catheter 105 and the mesh 125 has a second end 127 housed in the outer catheter 110 and coupled to a first end 116 of the deployment wire 115. In response to movement of the deployment wire 115, the mesh 125 is configured to move between a first position (see FIG. 1A) in an unexpanded condition having the form of a sheath to a second position (see FIG. 1B) in an expanded condition.

At least a portion of the mesh 125 can be composed of a pliable, MM-compatible, and biocompatible material. Suitable materials for the mesh 125 may include materials used to construct clot recovery devices, such as Solitare X™ by Medtronic, materials commonly used in stent devices, such as platinum chromium, or any other suitable implant material or combination of materials.

The mesh can cover the entirety of the inner catheter 105 and can be fixed at a second end 107 or tip of the inner catheter 105 by a suitable anchoring point in a ligation area (discussed below). Once inserted and placed in the treatment zone, such as the brain cavities (i.e., the ventricles), the mesh 125 may be deployed and expanded into the configuration of a balloon, for example, by advancing the deployment wire towards the first end 106 of the inner catheter 105. The mesh beneficially creates a barrier to prevent blockage of the fenestrations 108 and lumen 109 of the inner catheter 105 and may thereby reduce the need for revision surgeries.

The outer catheter 110 can provide a structural membrane configured to surround both the mesh 125 (before deployment) and the inner catheter 105, if needed, throughout nearly the entire length of the shunt apparatus 100, except for the first ends 126, 106, where the mesh 125 and the inner catheter 105, including fenestrations 108, are exposed. In other exemplary embodiments, the inner catheter 105 and outer catheter 110 can be positioned substantially parallel to one another and joined at least at their second ends 107, 112, if desired, and the inner dimensions of each can be suitably selected such that the inner catheter 105 can be smaller or the same size as the outer catheter, as desired.

In one optional implementation, the shunt apparatus 100 includes a ligation area 130 in the conduit 120 arranged external to the outer catheter 110 and configured to receive a fixation device 131. A portion of the conduit 120 may branch out from the outer catheter 110. In operation, once the mesh 125 has been placed and sized appropriately, the mesh 125 may be fixed in place by applying a fixation device 131 in the form of one or more clamps, sutures, staples, or a threaded screw in the ligation area 130. Alternatively, the fixation device 131 may be in the form of external intervention, such as electrocautery. In optional implementations, the conduit 120 may be sealed by the fixation device 131 to prevent drainage of CSF fluid, for example, through the conduit 120. The application of the fixation device 131 effectively locks the deployment wire 115 in place in the conduit 120 preventing further advancement or retraction of the mesh 125. Revision or removal of the shunt apparatus 100 can be achieved by relieving the aforementioned fixation device 131 at a transection point 132 and retracting the mesh 125.

In another optional implementation, the shunt apparatus 100 includes a coating of at least one of a pharmacologic agent or a therapeutic agent applied to a portion of at least one of the mesh 125 and the inner catheter 105. This coating may advantageously confer an additional function in select circumstances. Suitable coatings contemplated herein can include, for example, stem cells, anti-inflammatory agents, antibiotic agents, and drug delivery agents, among others. For example, the mesh 125 may be coated with an anticoagulant for VP shunt placement after an intraventricular hemorrhage to promote clot breakdown and prevent hematoma formation. The mesh 125 may also be coated with chemotherapeutics for the purpose of localized drug delivery after a ventricular tumor resection. Antibiotics may be applied onto the mesh 125 to reduce the rates of VP shunt infection, another significant cause of shunt revision/replacement. As such, the shunt apparatus 100 affords diverse avenues for targeted delivery of drugs and/or therapeutic compounds due to simplicity and strategic proximity to an otherwise inaccessible location of the brain, in example implementations.

Figure 1B:
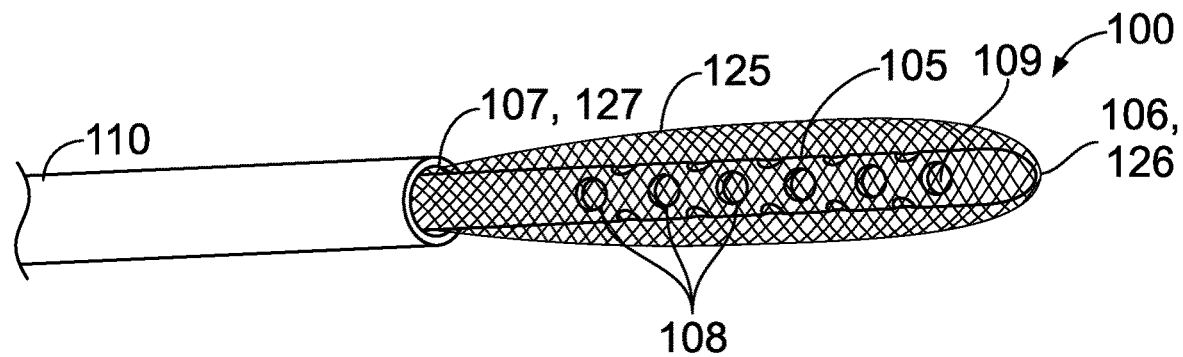
FIG. 1B is a side view of the shunt apparatus in a second position in an expanded condition, according to one example implementation.

In a further optional implementation, the mesh 125 has shape memory to assume a predetermined configuration in the expanded condition. In various implementations, the mesh 125 has a diameter in the expanded condition that increases as the first end 116 of the deployment wire 115 advances toward the first end 106 of the inner catheter 105. In additional implementations, the mesh 125 has a plurality of pores that increase in size as the first end 116 of the deployment wire 115 advances toward the first end 106 of the inner catheter 105. In other words, by either distancing or bringing together the first and second ends 126, 127 of the mesh 125, the "pores" become smaller or larger, respectively, and the diameter of the space within the mesh 125 likewise becomes smaller or larger, respectively. Still further, advancing or retracting the second end 127 of the mesh 125 via the deployment wire 115 will cause the mesh 125 to expand or contract and a desired geometry for the mesh 125 can thus be selected during insertion, as shown in FIGS. 1A and 1B.

In still another optional implementation, at least one memory foam portion may be coupled to the mesh 125 and configured to conform the mesh 125 to debris and brain parenchyma in a treatment zone.

Figure 2:
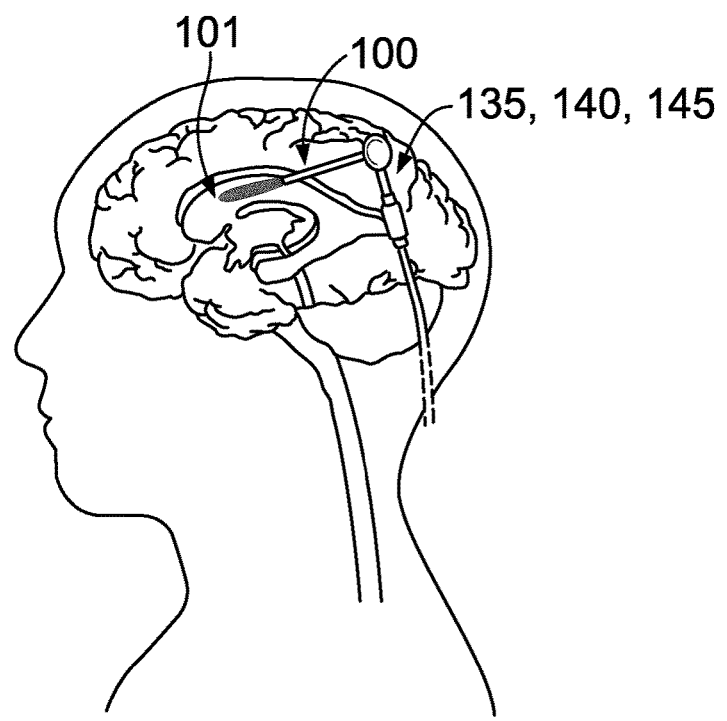
FIG. 2 is a side view of a treatment zone with the shunt apparatus deployed in a brain ventricle, the shunt apparatus couple to a valve system and a distal catheter, according to one example implementation.

In one optional implementation, as shown in FIG. 2, the shunt apparatus 100 includes a valve system 135 coupled to the outer catheter 110 and inner catheter 105. The valve system 135 is in fluid communication with the lumen 109 of the inner catheter 105. The shunt apparatus 100 can be configured to releasably connect to the valve system 135 that may include or be coupled to a shunt tubing system, or that can be custom designed to include flow control connectors, drug delivery connectors or other components, if desired.

In a further implementation, the shunt apparatus 100 includes a pressure sensor 140 coupled to the inner catheter 105 and configured to determine pressure from any CSF fluid in a lumen 109 of the inner catheter 105.

In yet another implementation, the shunt apparatus includes a processor 145 having a transceiver in electrical communication with the pressure sensor 140 and configured to send and receive signals to a remote computing device. For example, the processor may include a wireless component, such as a Bluetooth or near field communication (NFC) device for sending and receiving output signals to or from the pressure sensor component operably connected to the processor. Further, a database and algorithm can be configured for analyzing a signal received from the wireless component and providing a predictive output regarding the status of pressure in one or more selected locations near the shunt.

FIGS. 3A-B depicts the exemplary shunt apparatus 100 that illustrates the first position of the mesh 125 and the coupling or point of attachment to the deployment wire 115. Also shown is the ligation area 130 used to secure the mesh 125 after the mesh 125 advances to the second position having an expanded condition upon deployment. The conduit 120 is shown branching out from the outer catheter 110 with the deployment wire 115 residing therein and connected to the mesh 125. Once the shunt apparatus is placed in the treatment zone 101, the mesh 320 can be deployed by pushing the deployment wire 130 through the branched conduit 120 and then securing the deployment wire 130 by ligating the area 130 with a fixation device 131. If for any reason a revision should be needed, the conduit 120 can be cut more proximally to the ligation area 130, and the deployment wire 130 may be pulled back to retract the mesh (see FIG. 4E).

The following method 200 may include one or more operations, functions, or actions as illustrated by one or more of blocks 205-215. Although the blocks are illustrated in a sequential order, these blocks may also be performed in parallel, and/or in a different order than those described herein. Also, the various blocks may be combined into fewer blocks, divided into additional blocks, and/or removed based upon the desired implementation. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Referring now to FIG. 5, FIG. 5 shows a flowchart of an example method 200 for deploying the shunt apparatus 100, according to an example implementation. Method 200 includes, at block 205, advancing the first end 106 of the inner catheter 105 to a treatment zone 101. Then, at block 210, the deployment wire 115 is advanced toward the first end 106 of the inner catheter 105 and thereby advances the mesh 125 from the first position to the second position. For example, the mesh moves from a sheath to a balloon-like configuration. Next, at block 215, the deployment wire 115 is fixed in place via a fixation device 131 in a ligation area 130 in a conduit 120 that is arranged external to the outer catheter 110.

In one optional implementation, fixing the deployment wire 115 in place via the fixation device 131 in the ligation area 130 in the conduit 120 includes applying a plurality of staples or clips 131 to the conduit 120. In an alternative implementation, electrocautery may be used to seal the conduit 120 to the deployment wire 115.

In another optional implementation, prior to fixing the deployment wire 115 in place in the ligation area 130 of the conduit 120, a diameter of the mesh 125 is adjusted in the second position by at least one of advancing or retracting the deployment wire 115 relative to the first end 106 of the inner catheter 105. In addition, prior to fixing the deployment wire 115 in place in the ligation area 130 of the conduit 120, a size of a plurality of pores of the mesh 125 may be adjusted in the second position by one or more of advancing or retracting the deployment wire 115 relative to the first end 106 of the inner catheter 105.

In a further optional implementation, after fixing the deployment wire 115 in place in the ligation area 130 of the conduit 120, the conduit 120 and deployment wire 115 are transected proximal to the ligation area 130 (i.e., between the ligation area 130 and the outer catheter 110) and thereby access to the deployment wire is obtained. Then, the deployment wire 115 is retracted away from the first end 106 of the inner catheter 105 and thereby the mesh 125 is returned to the first position. In a further implementation, the shunt apparatus 100 may then be removed from the treatment zone 101.

In one optional implementation, the deployment wire is advanced toward the first end 106 of the inner catheter 105 includes advancing the deployment wire 115 a predetermined distance. This predetermined distance may correspond to a known or desired diameter or geometry of the mesh 125.

In one optional implementation, the outer catheter 110 and inner catheter 105 are coupled to a valve system 135, such that the valve system 135 is in fluid communication with the lumen 109 of the inner catheter 105. This valve system may aid in draining CSF fluid, for example to a distal catheter away from the brain. In a further optional implementation, detecting, via a pressure sensor 140 coupled to the inner catheter detects a pressure in a lumen 109 of the inner catheter 105. Then, a processor 145 having a transceiver in electrical communication with the pressure sensor 140 sends a signal indicating a detected pressure to a remote computing device. Next, the processor 140 receives a signal from the remote computing device indicating whether to open or close the value system 135.

Figure 4A:
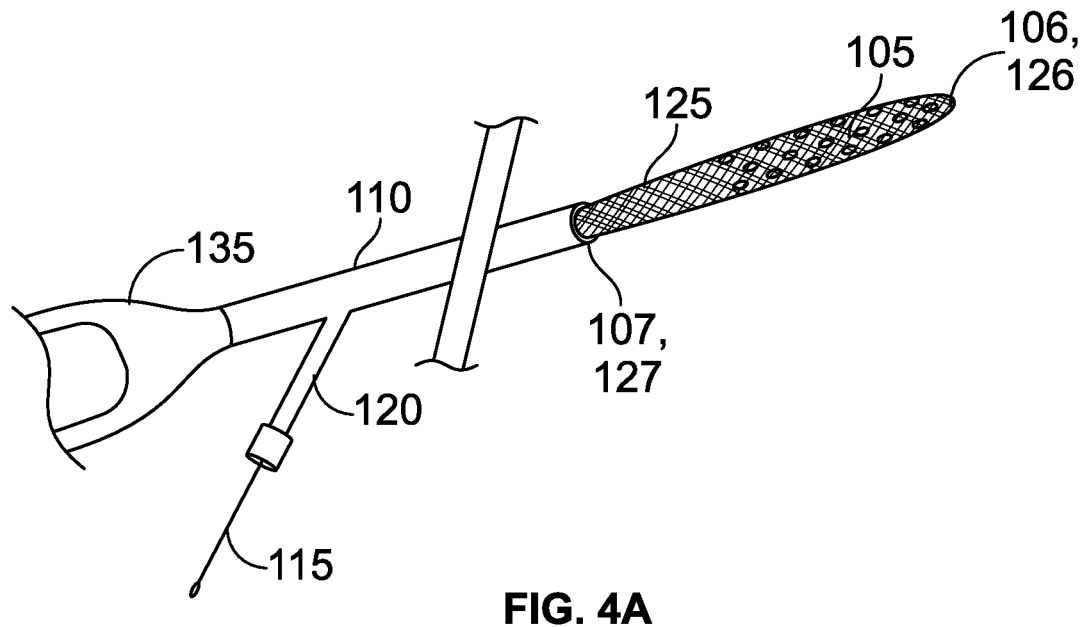
FIG. 4B shows a side view of the shunt apparatus in a second position in an expanded condition, according to one example implementation
FIG. 4C shows a side view of the shunt apparatus with the deployment wire fixed in place via a fixation device in a ligation area in a conduit that is arranged external to the outer catheter, according to one example implementation.
FIG. 4D shows a side view of the shunt apparatus with the conduit and wire transected proximal to the ligation area, according to one example implementation.
FIG. 4E shows a side view of the shunt apparatus after the mesh has returned to the first unexpanded state from the second expanded state, according to one example implementation.

FIGS. 4A-E show various states of the shunt apparatus 100 when used in the exemplary method of deployment 200. FIG. 4A illustrates the shunt apparatus 100 in the first position in the form of a sheath in an unexpanded state. The shunt apparatus may be placed intracranially in this first position with the deployment wire 115 fully retracted After deployment, the shunt apparatus 100 can be connected to the valve system 135.

Figure 4B:
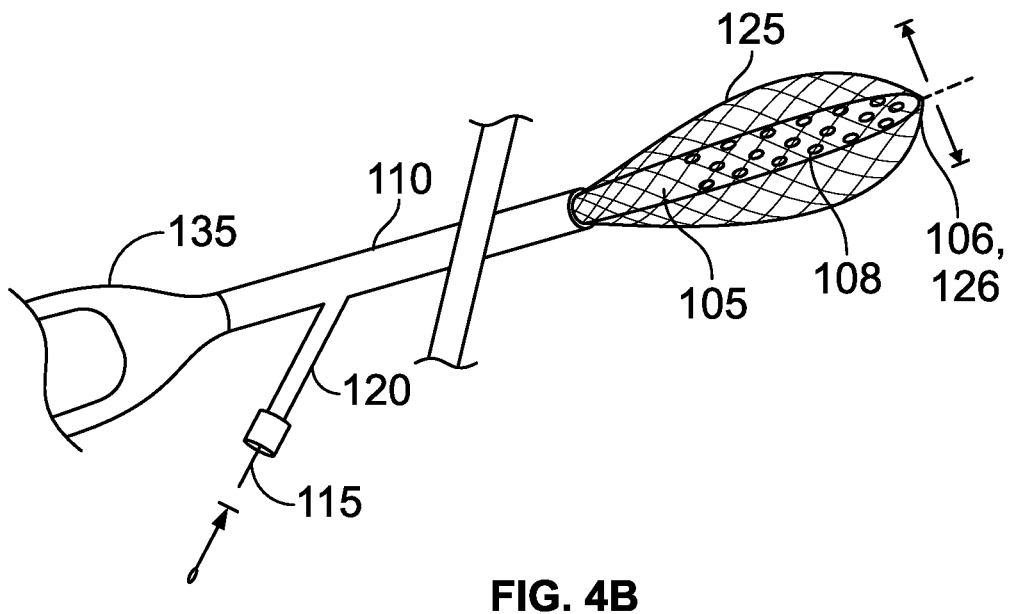

FIG. 4B shows that, once proper placement of the shunt apparatus 100 has been achieved in the treatment zone 101, the mesh 125 is expanded by threading the deployment wire 115 in through the conduit 120 by a preset length, for example. The mesh 125 is fixed at the first end 106 of the inner catheter 105, thereby allowing the mesh 125 to expand outwards from the inner catheter 105 upon advancement of the deployment wire 115.

Figure 4C:
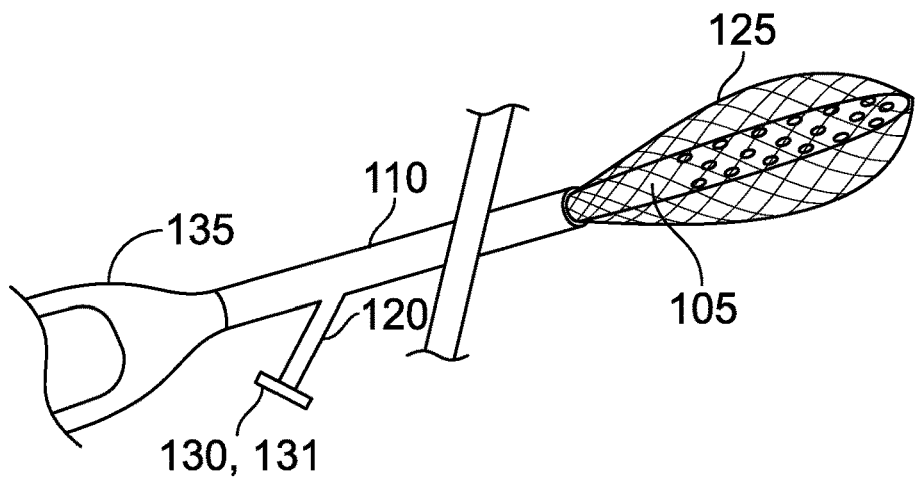

FIG. 4C shows that the deployment wire 115 may then be secured at a ligation area 130 via a fixation device 131 to prevent slippage or movement that could further expand the mesh 125 to an or retract the mesh 125 to a undesirable size.

Figure 4D:
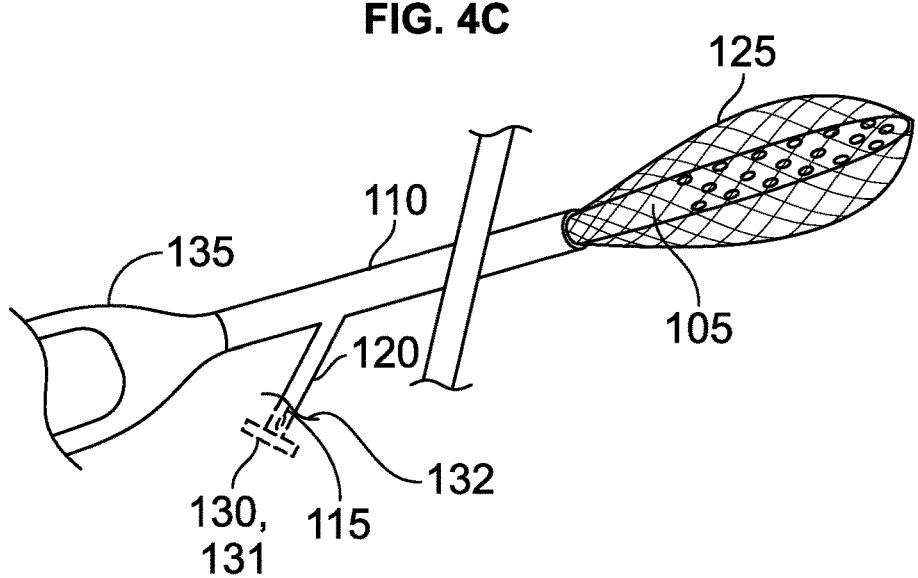

FIG. 4D shows removal or revision of the shunt apparatus 100. Here, the branched conduit 120 may be transected or cut at any point between the ligation area 130 and the outer catheter 110, thereby exposing the deployment wire 115 for retraction.

Figure 4E:
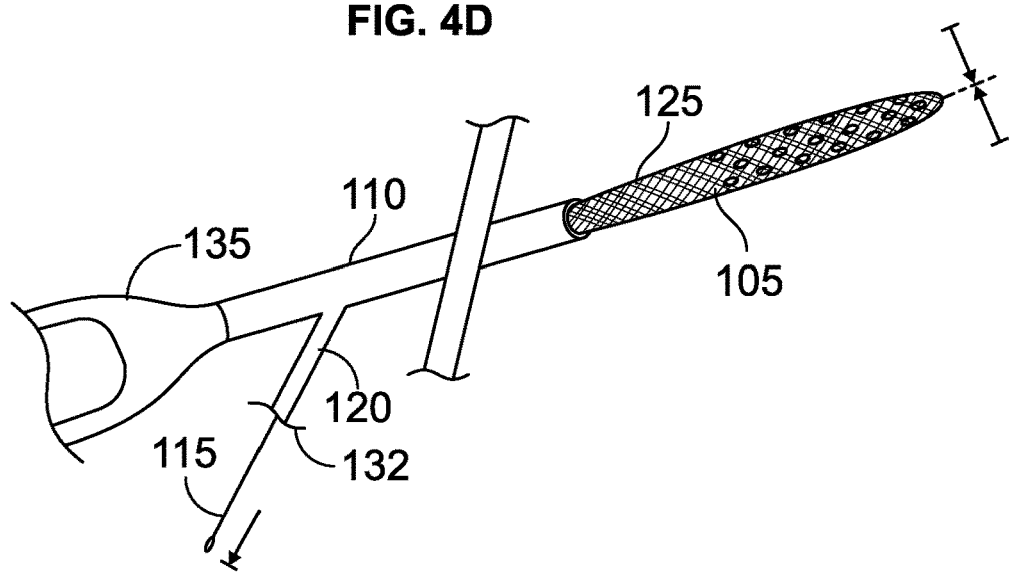

FIG. 4E shows that the wire 115 can then be pulled back or retracted causing the previously expanded mesh 125 to retract and contract into its original sheath-like configuration. The shunt apparatus 100 may then be removed from the treatment zone 101, such as a ventricle of the brain. The unexpanded first position of the mesh 125 may be able to minimize trauma to the treatment zone 101 (e.g., the brain parenchyma) during removal.

Other embodiments, components and materials consistent with the principles herein are contemplated as well.

The invention claimed is:

1. A shunt apparatus, comprising:
   an inner catheter having a first end and a second end, wherein the inner catheter has a plurality of fenestrations extending along a portion of the first end of the inner catheter and in fluid communication with a lumen of the inner catheter;
   an outer catheter, wherein the inner catheter is positioned at least partially within a lumen of the outer catheter;
   a deployment wire moveably arranged in a lumen of a conduit that is coupled to the outer catheter, wherein the lumen of the conduit is in communication with the lumen of the outer catheter such that a portion of the deployment wire is moveable within the outer catheter; and
   a mesh arranged surrounding at least the first end of the inner catheter, wherein the mesh has a first end fixedly coupled to a proximal tip of the first end of the inner catheter and the mesh has a second end housed in the outer catheter and coupled to a first end of the deployment wire, wherein, in response to movement of the deployment wire, the second end of the mesh is configured to advance through the outer catheter and the mesh is configured to move between a first position in an unexpanded condition having the form of a sheath to a second position in an expanded condition.

2. The shunt apparatus of claim 1, further comprising a ligation area in the conduit arranged external to the outer catheter and configured to receive a fixation device.

3. The shunt apparatus of claim 1, further comprising a coating of at least one of a pharmacologic agent or a therapeutic agent applied to a portion of at least one of the mesh and the inner catheter.

4. The shunt apparatus of claim 1, wherein the mesh has shape memory to assume a predetermined configuration in the expanded condition.

5. The shunt apparatus of claim 1, wherein the mesh has a diameter in the expanded condition that increases as the first end of the deployment wire advances toward the first end of the inner catheter.

6. The shunt apparatus of claim 1, wherein the mesh has a plurality of pores that increase in size as the first end of the deployment wire advances toward the first end of the inner catheter.

7. The shunt apparatus of claim 1, further comprising:
   a valve system coupled to the outer catheter and inner catheter, the valve system in fluid communication with the inner catheter.

8. The shunt apparatus of claim 1, further comprising:
   at least one memory foam portion coupled to the mesh and configured to conform the mesh to debris and brain parenchyma.

9. The shunt apparatus of claim 8, further comprising:
   a pressure sensor coupled to the inner catheter and configured to determine pressure from any CSF fluid in a lumen of the inner catheter.

10. The shunt apparatus of claim 9, further comprising:
    a processor having a transceiver in electrical communication with the pressure sensor and configured to send and receive signals to a remote computing device.

11. A method for deploying the shunt apparatus of claim 1, the method comprising:
    advancing the first end of the inner catheter to a treatment zone;
    advancing the deployment wire toward the first end of the inner catheter and thereby advancing the mesh from the first position to the second position; and
    fixing the deployment wire in place via a fixation device in a ligation area in a conduit that is arranged external to the outer catheter.

12. The method of claim 11, wherein fixing the deployment wire in place via the fixation device in the ligation area in the conduit comprises applying a plurality of staples or clips to the conduit.

13. The method of claim 11, wherein fixing the deployment wire in place via the fixation device in the ligation area in the conduit comprises using electrocautery to seal the conduit to the deployment wire.

14. The method of claim 11, further comprising:
    prior to fixing the deployment wire in place in the ligation area of the conduit, adjusting a diameter of the mesh in the second position by at least one of advancing or retracting the deployment wire relative to the first end of the inner catheter.

15. The method of claim 11, further comprising:
    prior to fixing the deployment wire in place in the ligation area of the conduit, adjusting a size of a plurality of pores of the mesh in the second position by one or more of advancing or retracting the deployment wire relative to the first end of the inner catheter.

16. The method of claim 11, further comprising:
after fixing the deployment wire in place in the ligation area of the conduit, transecting the conduit and deployment wire proximal to the ligation area and thereby obtaining access to the deployment wire; and
retracting the deployment wire away from the first end of the inner catheter and thereby returning the mesh to the first position.

17. The method of claim 16, further comprising:
removing the shunt apparatus from the treatment zone.

18. The method of claim 11, wherein advancing the deployment wire toward the first end of the inner catheter comprises advancing the deployment wire a predetermined distance.

19. The method of claim 11, further comprising:
coupling the outer catheter and inner catheter to a valve system, such that the valve system is in fluid communication with the inner catheter.

20. The method of claim 19, further comprising:
detecting, via a pressure sensor coupled to the inner catheter, a pressure in a lumen of the inner catheter;
sending, via a processor having a transceiver in electrical communication with the pressure sensor, a signal indicating a detected pressure to a remote computing device; and
receiving, via the processor, a signal from the remote computing device indicating whether to open or close the value system.

\* \* \* \* \*